(12) United States Patent
Deininger et al.

(10) Patent No.: US 11,491,339 B2
(45) Date of Patent: Nov. 8, 2022

(54) SEALS FOR LEAD BORES OF IMPLANTABLE MEDICAL DEVICES

(71) Applicant: MEDTRONIC, INC., Minneapolis, MN (US)

(72) Inventors: Steven T. Deininger, Plymouth, MN (US); Jeffrey Clayton, Zimmerman, MN (US); Thomas M. Hillebrand, Minneapolis, MN (US); Jenna George, Edina, MN (US); Bin Wang, Maple Grove, MN (US); Michael T. Hegland, Mounds View, MN (US); Darren A. Janzig, Center City, MN (US); Sean P. Skubitz, Forest Lake, MN (US); Richard T. Stone, Minneapolis, MN (US); Dale F. Seeley, Spring Park, MN (US); Salil M. Vaidya, Maharashtra (IN)

(73) Assignee: MEDTRONIC, INC., Minneapolis, MN (US)

( * ) Notice: Subject to any disclaimer, the term of this patent is extended or adjusted under 35 U.S.C. 154(b) by 833 days.

(21) Appl. No.: 16/396,474

(22) Filed: Apr. 26, 2019

(65) Prior Publication Data

US 2020/0338355 A1 Oct. 29, 2020

(51) Int. Cl.
*A61N 1/375* (2006.01)
*H01R 13/52* (2006.01)

(52) U.S. Cl.
CPC ......... *A61N 1/3754* (2013.01); *H01R 13/521* (2013.01); *H01R 13/5224* (2013.01)

(58) Field of Classification Search
CPC .............. H01R 13/5224; H01R 13/521; H01R 13/5205; A61N 1/3754; A61N 1/3752
See application file for complete search history.

(56) References Cited

U.S. PATENT DOCUMENTS

| | | | | |
|---|---|---|---|---|
| 6,029,089 | A | * | 2/2000 | Hawkins .............. A61N 1/3752 439/271 |
| 10,092,762 | B2 | | 10/2018 | Jiang et al. |
| 2007/0100386 | A1 | * | 5/2007 | Tronnes ............... A61N 1/3752 607/37 |

(Continued)

FOREIGN PATENT DOCUMENTS

WO 2018102042 7/2018

OTHER PUBLICATIONS

PCT/US2020/027628 International Search Report and Written Opinion, dated Jul. 10, 2020.

*Primary Examiner* — Timothy J Thompson
*Assistant Examiner* — Rhadames Alonzo Miller
(74) *Attorney, Agent, or Firm* — Withers & Keys, LLC

(57) ABSTRACT

Seals used within lead bores of implantable medical devices for creating a seal to implantable medical leads inserted into the lead bores include an inner cylinder that engages the lead body. The inner cylinder is surrounded by a gap to either an outer cylinder of the seal or to surrounding structures of the implantable medical device. The inner cylinder has freedom of movement within the gap such that movement of the lead body that is off-axis relative to a centerline of the lead bore causes movement of the inner cylinder that is providing the seal. In this manner, the seal engagement to the lead body is maintained during this off-axis movement of the lead body.

32 Claims, 18 Drawing Sheets

(56) References Cited

U.S. PATENT DOCUMENTS

| | | | |
|---|---|---|---|
| 2007/0225772 A1* | 9/2007 | Lahti | A61N 1/3752 607/37 |
| 2010/0123291 A1* | 5/2010 | Dilmaghanian | F16J 15/025 264/318 |
| 2010/0267265 A1* | 10/2010 | Dilmaghanian | H01R 24/58 439/271 |
| 2011/0059639 A1* | 3/2011 | Dilmaghanian | H01R 24/58 439/271 |
| 2011/0160678 A1* | 6/2011 | Chong | A61M 5/1413 29/428 |
| 2012/0065625 A1* | 3/2012 | Nelson | A61M 39/12 604/533 |
| 2016/0045311 A1* | 2/2016 | McCann | A61F 2/2412 623/2.11 |
| 2017/0231738 A1 | 8/2017 | Severson | |
| 2019/0192861 A1* | 6/2019 | Lopez | A61N 1/36128 |
| 2019/0314635 A1* | 10/2019 | Iyer | H01R 13/5224 |

* cited by examiner

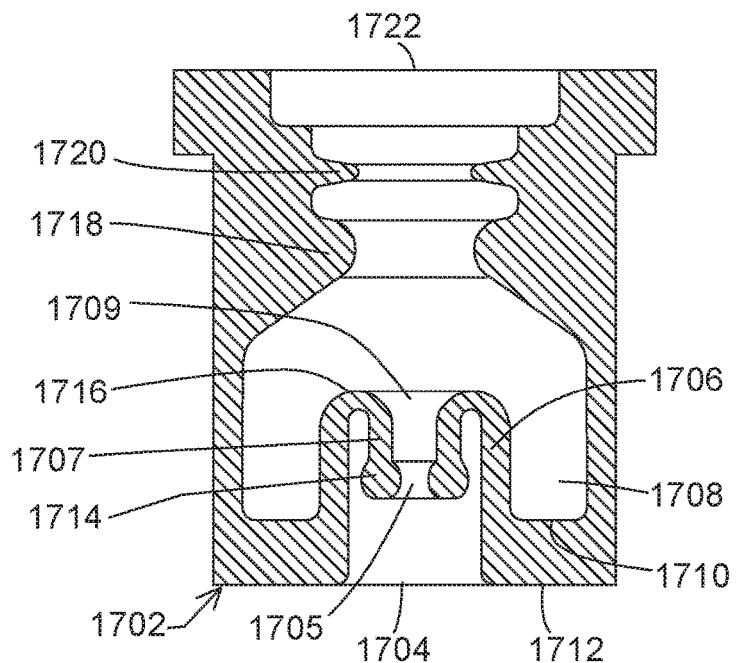
FIG. 24
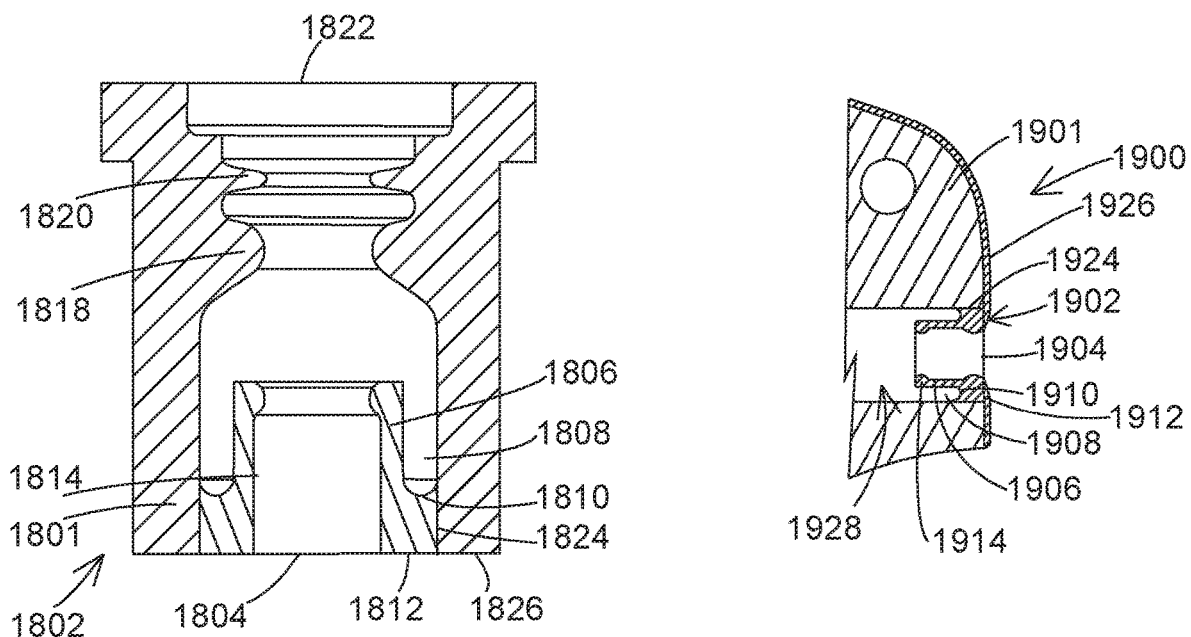
FIG. 25
FIG. 26

SEALS FOR LEAD BORES OF IMPLANTABLE MEDICAL DEVICES

TECHNICAL FIELD

Embodiments relate to seals that are placed in lead bores of implantable medical devices.

BACKGROUND

A lead bore of implantable medical device includes one or more electrical connectors that make an electrical connection to corresponding electrical contacts on a proximal end of an implantable medical lead that is inserted into the lead bore. Conductors within the implantable medical lead carry electrical signals between the electrical contacts and electrodes located near a distal end of the lead. These electrical signals may be stimulation signals being delivered to tissue at the distal electrodes. These signals may additionally or alternatively be sensed physiological signals occurring at the distal electrode that are delivered to the sensing circuitry of the implantable medical device.

When carrying stimulation signals or sensed signals on the implantable medical lead, it is useful to electrically isolate the electrical contacts on the proximal end from each other as well as from the body tissue surrounding the implantable medical device. For instance, such isolation helps a signal intended for a given proximal contact and corresponding distal electrode to be delivered to that proximal contact and distal electrode while largely preventing any amount of the signal from leaking to the body or other proximal contact at the proximal end of the lead. Likewise, such isolation helps a sensed signal obtained at a given distal electrode to be delivered to the circuit path of the implantable device corresponding to the proximal contact paired to that distal electrode while largely preventing any amount of the signal from leaking to the body or other proximal contact at the proximal end of the lead. Likewise, other electrical signals present nearby the implantable medical device may be largely blocked from leaking into the lead bore.

Electrical isolation is provided by the presence of seals within the lead bore of the implantable medical device. These seals typically are present between adjacent electrical connectors within the lead bore and also at the lead bore entrance at the surface of the implantable medical device. These seals may generally provide circumferential protrusions with an open center that has a smaller diameter than the lead diameter so that contact is made at the open center with the lead body to provide a seal about the lead body.

While a seal is formed, movement of the lead body in radial directions may stretch the opening of the protrusions which may form a small gap that allows small amounts of body fluid to pass by the seal. This lead body movement may occur during implantation or during normal body movement by the patient. While the small amount of fluid may not always be a concern, for situations where the electrical signals of interest are already very small yet other nearby signals are large, such as when a relatively small neurological signal of the brain is being sensed while relatively large cardiac signals are present near the implantable medical device, a small amount of fluid ingress to the lead bore may cause enough signal leakage to be problematic.

SUMMARY

Embodiments address issues such as these and others by providing a seal for an implantable medical device that includes a cylindrical portion that engages the lead body where the cylindrical portion has a freedom of movement relative to a portion of the seal that remains in a fixed position with the lead bore. Rather than a point of contact to the lead body created by a radially inward protrusion that has a fixed position, the cylindrical portion extends along a length of the lead body so that during movement of the lead body in radial directions, the cylindrical portion also moves to maintain contact with the lead body.

Embodiments provide a seal for an implantable medical device that comprises a body. The body comprises a first cylinder that is elastic and that defines a seal bore having a centerline, the first cylinder having an outer diameter. The body further comprises a wall portion that is coupled to the first cylinder and that has an outer surface that forms a plane that the centerline intersects, the first cylinder being movable relative to the wall portion to allow an angle of intersection between the centerline and the plane to change.

Embodiments provide an implantable medical device that comprises a housing defining a lead bore having a lead bore diameter and circuitry within the housing. The implantable medical device further comprises an electrical connector positioned within the lead bore and electrically coupled to the circuitry and a seal body coupled to the housing. The seal body comprises a first cylinder that is elastic and that defines a seal bore having a centerline, the first cylinder being positioned within the lead bore and having an outer diameter that is smaller than the lead bore diameter at a position of the first cylinder. The seal body further comprises a wall portion that is coupled to the housing, the wall portion being coupled to the first cylinder and having an outer surface that forms a plane that the centerline intersects, the first cylinder being movable relative to the wall portion to allow an angle of intersection between the centerline and the plane to change.

Embodiments provide a seal for an implantable medical device that comprises a body. The body comprises a first cylinder that is elastic and that defines a seal bore having a centerline, the first cylinder having an outer diameter. The body further comprises a wall portion that is coupled to the first cylinder with the first cylinder having a resting position where the centerline forms a first angle with respect to a first plane, the first cylinder being movable relative to the wall portion to allow the first angle of the centerline with respect to the first plane to change.

Embodiments provide an implantable medical device that comprises a housing defining a lead bore having a lead bore diameter and circuitry within the housing. The implantable medical device further comprises an electrical connector positioned within the lead bore and electrically coupled to the circuitry and a seal body coupled to the housing. The seal body comprises a first cylinder that is elastic and that defines a seal bore having a centerline, the first cylinder being positioned within the lead bore and having an outer diameter that is smaller than the lead bore diameter at a position of the first cylinder. The seal body further comprises a wall portion that is coupled to the housing, the wall portion being coupled to the first cylinder with the first cylinder having a resting position where the centerline forms a first angle with respect to a first plane, the first cylinder being movable relative to the wall portion to allow the first angle of the centerline with respect to the first plane to change.

The embodiments described herein are discussed primarily in regard to a header mounted to a housing of an implantable medical device for accepting a proximal end of a lead. However, this should not be considered a limitation. The described seal elements may be incorporated into any aspect of an implantable system that requires a seal element that couples to a movable member that may move relative to a wall portion of the seal element. For example, this type of seal element may likewise be employed at a distal end of a lead extension having a lead bore that receives a proximal end of a lead.

DESCRIPTION OF THE DRAWINGS

FIG. 24 shows a cross-sectional top view of a seventeenth example where the inner cylinder is coupled to a rear wall and acquires an inversion as the lead body travels through the inner cylinder.

FIG. 25 shows a cross-sectional top view of an eighteenth example where the inner cylinder and the outer cylinder are separate pieces that are bonded together.

FIG. 26 shows a cross-sectional side view of a front portion of a header that includes an example of the seal where the inner cylinder is bonded directly to the lead bore of the header.

DETAILED DESCRIPTION

Embodiments provide seals for lead bores of implantable medical devices and/or lead extensions that allow the lead to move radially out of center-alignment relative to the lead bore while maintaining a sealing engagement to a lead body of the lead.

Figure 1:
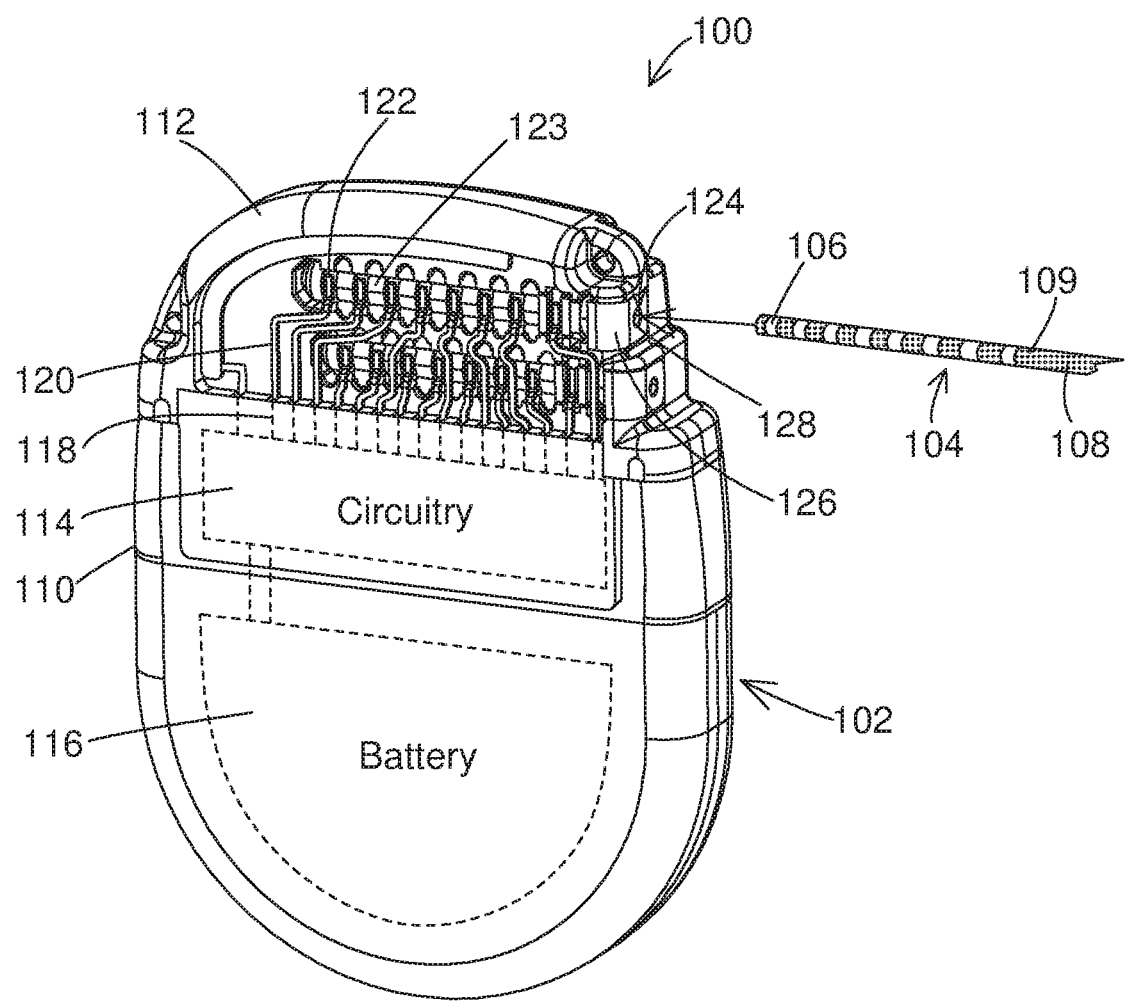
FIG. 1 shows an example of an implantable medical system including an implantable medical lead and an implantable medical device that may include seals according to the various embodiments.
Figure 2:
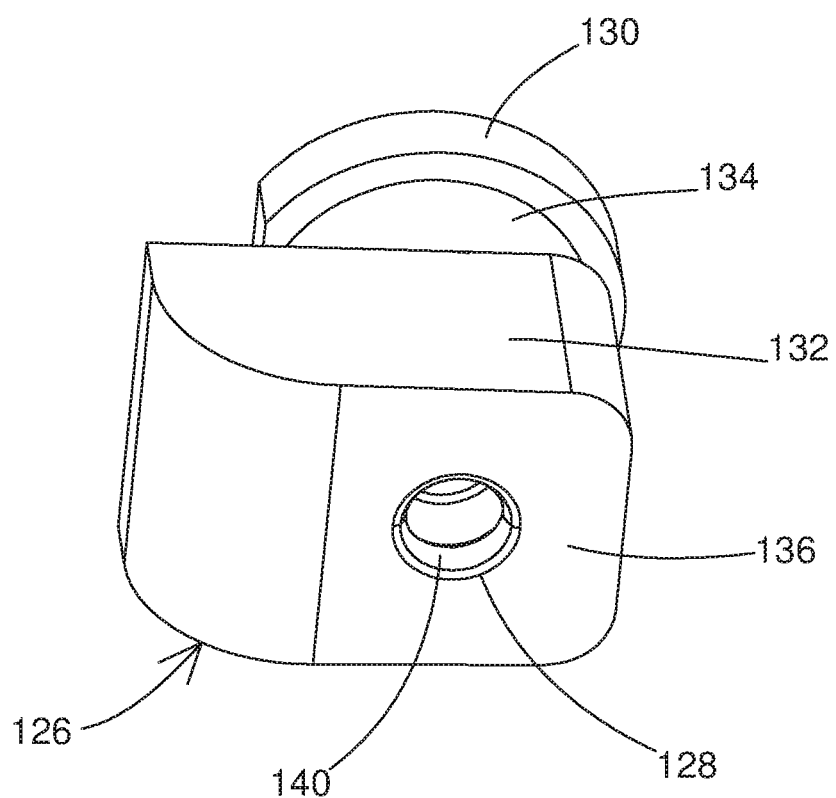
FIG. 2 shows a front view of an example of a seal that may be used in an implantable medical device.

FIG. 1 shows an implantable medical system 100 that includes an implantable medical device 102 and an implantable medical lead 104. The implantable medical device 102 includes a circuitry housing 110 and a header 112 mounted to the circuitry housing 110 that together form a complete device housing. The circuitry housing 110 provides a sealed enclosure for circuitry 114 and an associated battery 116 that powers the circuitry. The circuitry 114 may include a stimulation engine capable of producing stimulation pulses. The circuitry 114 may also or alternatively include a sensing circuit capable of receiving physiological signals. Examples of the implantable medical device 102 include but are not limited to neurostimulators such as those for deep brain, spinal cord, pelvic, or peripheral nerve sensing and/or stimulation. Such a device may be used to deliver electrical stimulation therapy and, in some case, also deliver a therapeutic agent, to various tissue sites of a patient to treat a variety of symptoms or conditions such as chronic pain, tremor, Parkinson's disease, other movement disorders, epilepsy, urinary or fecal incontinence, sexual dysfunction, obesity, or gastroparesis. In other examples, such a device may be a cardiac device used to deliver electrical stimulation to the heart.

In order to deliver the electrical signals, the circuitry 114 has electrical connections 118 that establish electrical pathways to conductors 120 present within the header 112. The electrical connections 118 may include feedthroughs that allow the electrical pathways to transition between the interior of the circuitry housing 110 and the interior of the header 112 while maintaining a sealed relationship between the circuitry housing 110 and the header 112.

The header 112 provides a lead bore 124 that includes a set of electrical connectors 122. The conductors 120 are electrically coupled to the corresponding electrical connectors 122 to deliver the electrical signals. The lead bore 124 also includes a set of seals 123 that are interleaved with the electrical connectors 122. A front seal 126 of this example also provides an exterior surface for the header 112 in the area at the opening of the lead bore 124. In this particular example, there is a second lead bore also containing electrical connectors with interleaved seals. While the conductors 120, electrical connectors 122, and seals 123 are visible in FIG. 1, they are enclosed in a sealed arrangement with the header 112 by a layer of liquid silicone rubber or other similar material.

A proximal end of the implantable medical lead 104 is shown. On this proximal end, the lead includes proximal contacts 106 mounted to a lead body 108. These proximal contacts are conductors such as metal rings. Conductors inside the lead body 108 electrically couple the proximal contacts 106 to distal electrodes located on the distal end of the lead 104.

The proximal end of the lead 104 is inserted into the lead bore 124 of the implantable medical device 102 and/or lead extension. Each proximal contact 106 electrically couples to a corresponding electrical connector 122. Each seal 123 engages the lead body 108 between adjacent proximal contacts 106. The front seal 126 engages the lead body 108 distally of the most-distal proximal contact 106. In this example, because the front seal 126 provides an outer surface of the header 112 at the lead bore 124, the front seal 126 includes an opening 128. This example of the lead 104 also includes a surface coating 109, such as a siloxane or parylene coating, that reduces friction as the lead body 108 passes through the front seal 126. This surface coating 109 may be effective for certain configurations of the front seal 126, such as the examples shown in FIGS. 13-17 that are discussed in more detail below.

FIGS. 2-6 show various perspective and cross-sectional views of the front seal 126. The front seal is at least in part an elastic body that includes at least a portion that is compliant in order to receive the lead body 108 and create a seal against the lead body 108. Examples of elastic materials suitable for the front seal 126, or the elastic portion of the front seal 126 if not wholly elastic, include biocompatible materials having a modulus of elasticity value, such as specified in the datasheet document entitled SILASTIC® BioMedical Grade Liquid Silicone Rubbers, from Dow Corning Corporation, Copyright 2002-2006, in the range of 100 to 1000 pounds per square inch, or in another example in the range of 400 to 700 pounds per square inch. Examples of suitable biocompatible materials include but are not limited to silicones and urethanes.

The opening 128 of the front seal 126 is present on a front wall portion 136 that provides an exterior surface. In this example, the exterior surface of the front wall portion 136 defines a plane, such as the plane discussed below in relation to FIGS. 7B and 8B. However, in other examples, the exterior surfaces of the front seal 126 may not be planar. In this example, the front seal 126 also includes a front block 132 followed by a rear cylinder 134 and rear flange 130. The rear flange 130, rear cylinder 134, and block 132 may engage corresponding receptacles in the header 112 to thereby fix the proper position of the front seal 126 relative to the header 112.

Figure 3:
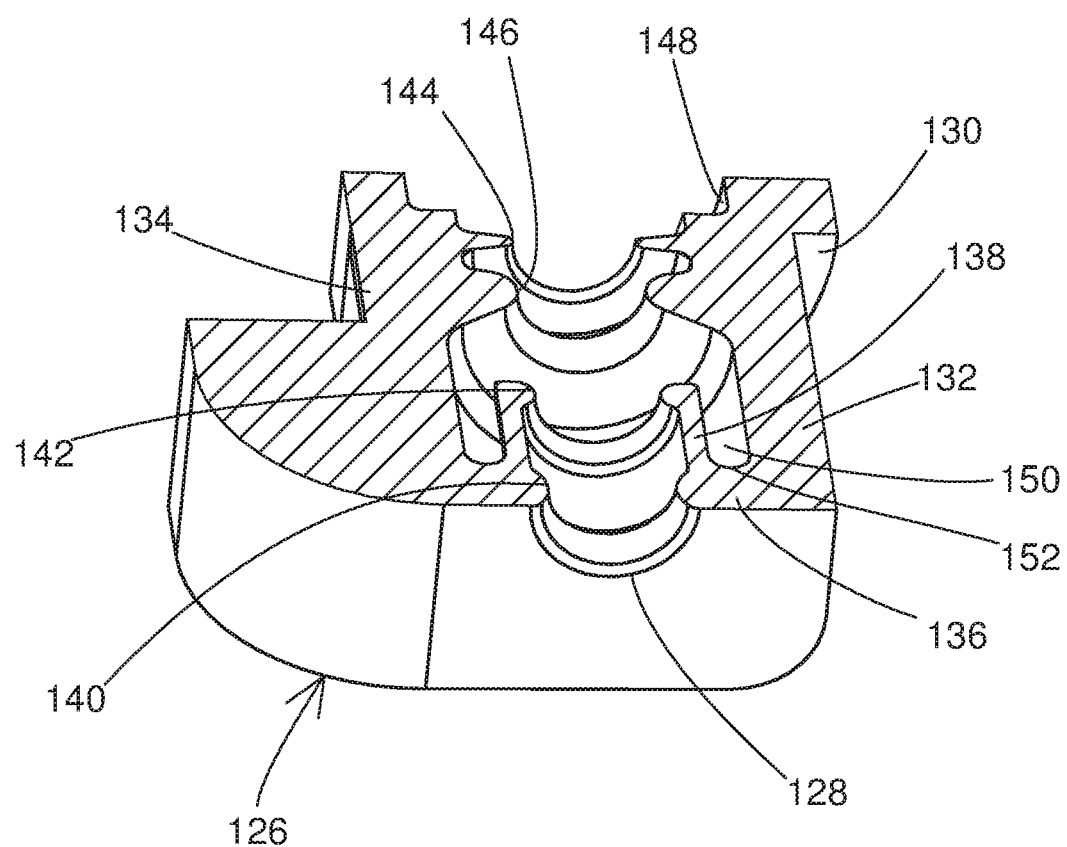
FIG. 3 shows a cross-sectional front view of the seal of FIG. 2 that illustrates an inner cylinder present within the seal.
Figure 4:
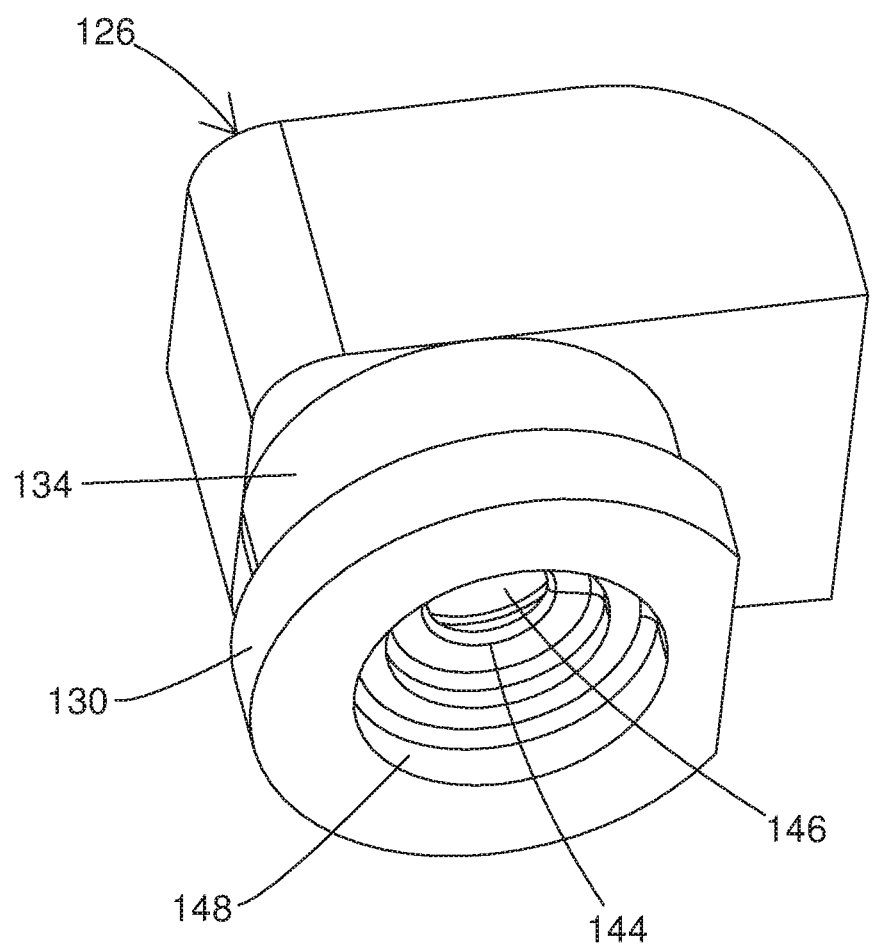
FIG. 4 shows a rear view of the seal of FIG. 2.
Figure 5:
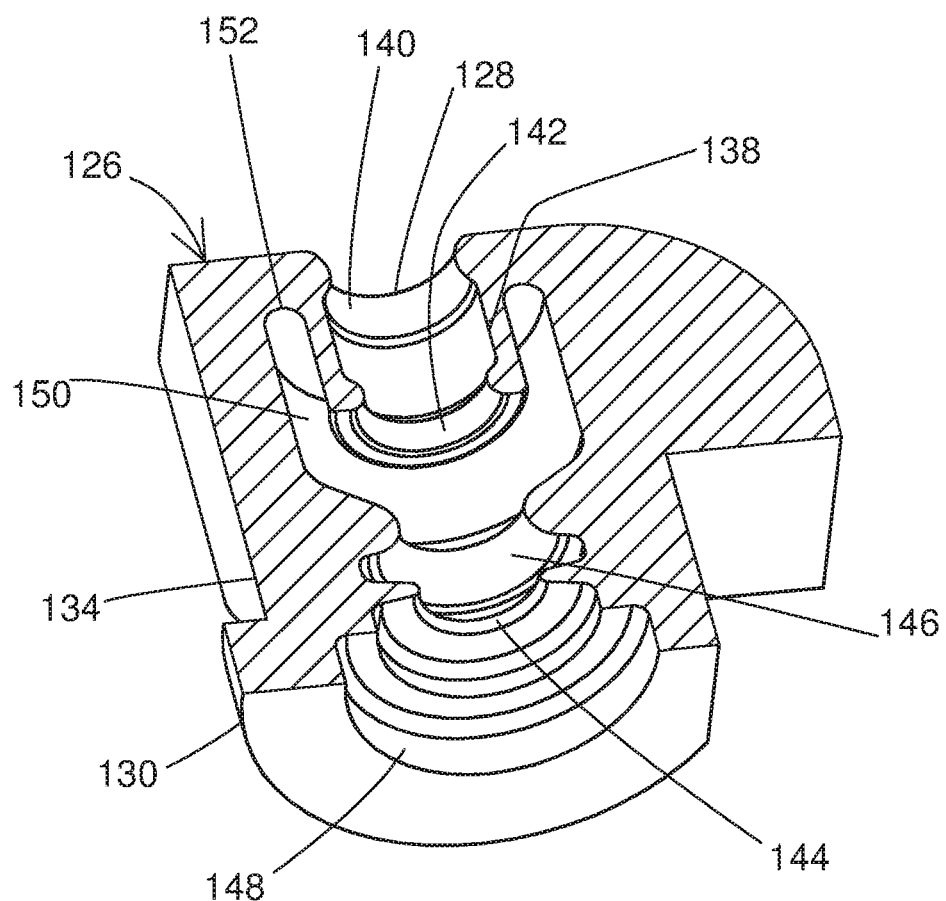
FIG. 5 shows a cross-sectional rear view of the seal of FIG. 2.
Figure 6:
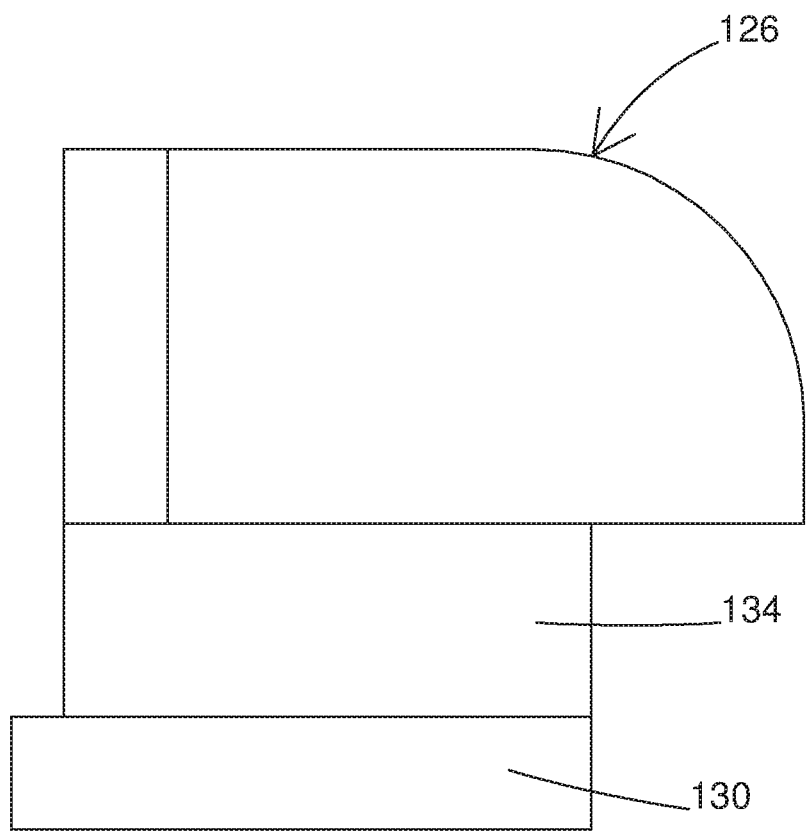
FIG. 6 shows a top view of the seal of FIG. 2.

As best shown in the cross-sectional views of FIGS. 3 and 5, the front seal 126 includes several internal features. An inner cylinder 138 is present at the opening 128 and this inner cylinder defines a seal bore through which the lead body 108 is placed. The inner cylinder 138 is attached at a front end to the front wall 126. The block 132 forms an outer cylinder that is coupled to the wall portion 136 and defines an outer seal bore. The block 132 is separated from the inner cylinder 138 by a gap 150 due to the outer seal bore created by the block 132 having an inner diameter that is greater than the outer diameter of the inner cylinder 138. In this example, the inner cylinder 138 and outer cylinder of block 132 are concentric such that the gap 150 is a consistent size around the circumference but may be non-concentric in other examples.

The wall portion 136 defines a transition portion 152 between the end of the inner cylinder 138 and the end of the outer cylinder defined by the block 132. Because the rear end of the inner cylinder 138 is unattached, the transition portion 152 serves as a hinge-like connection of the inner cylinder 138 to the wall portion 136 and block 132. As the front seal 126 is at least partially an elastic body, the transition portion 152 allows the rear end of the inner cylinder 138 to have freedom of movement within the gap 150 which allows the inner cylinder 138 to remain in sealing engagement with the lead body 108 as the lead body 108 may move about.

In some examples, including the one shown in FIGS. 2-8, seal protrusions 144 and 146 that extend inward radially into the outer seal bore of block 132 may be provided rearward of the inner cylinder 138 to further seal and support the lead body 108. However, such protrusions 144, 146 may be subject to forming a gap with respect to the lead body 108 upon movement of the lead body 108 in various radial directions but the presence of the inner cylinder 138 prevents leakage that might otherwise occur through such gaps. This phenomenon is shown in FIGS. 7A-8B and discussed below.

In the example shown in FIGS. 2-8B, the opening 128 provides a sealing protrusion 140. The inner cylinder 138 of the front seal 126 also includes an additional relatively small protrusion 142 in a rearward location. Because the inner cylinder 138 has a freedom of movement with respect to the remainder of the front seal 126, the protrusion 142 remains fully engaged about the circumference of the lead body 108 during radial movement.

Figure 7A:
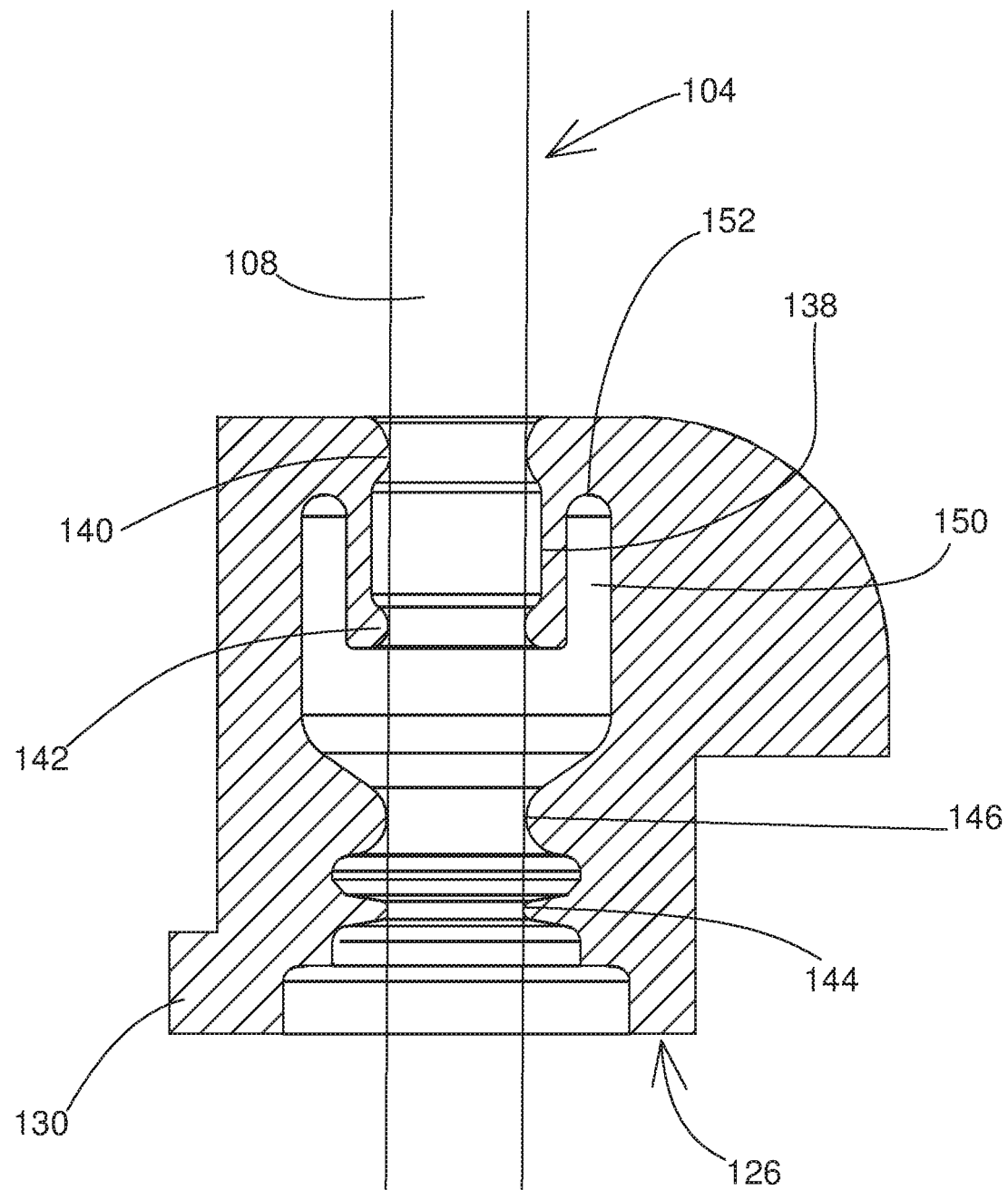
FIG. 7A shows a cross-sectional top view of the seal of FIG. 2 and further shows a lead body being center-aligned within the seal.

FIG. 7A shows the lead body 108 present within the front seal 126. Here, the lead body 108 is center-aligned within the front seal 126. Therefore, all sealing engagements including protrusion 140, inner cylinder protrusion 142, protrusion 144, and protrusion 146 are making complete circumferential engagement to the lead body 108.

Figure 7B:
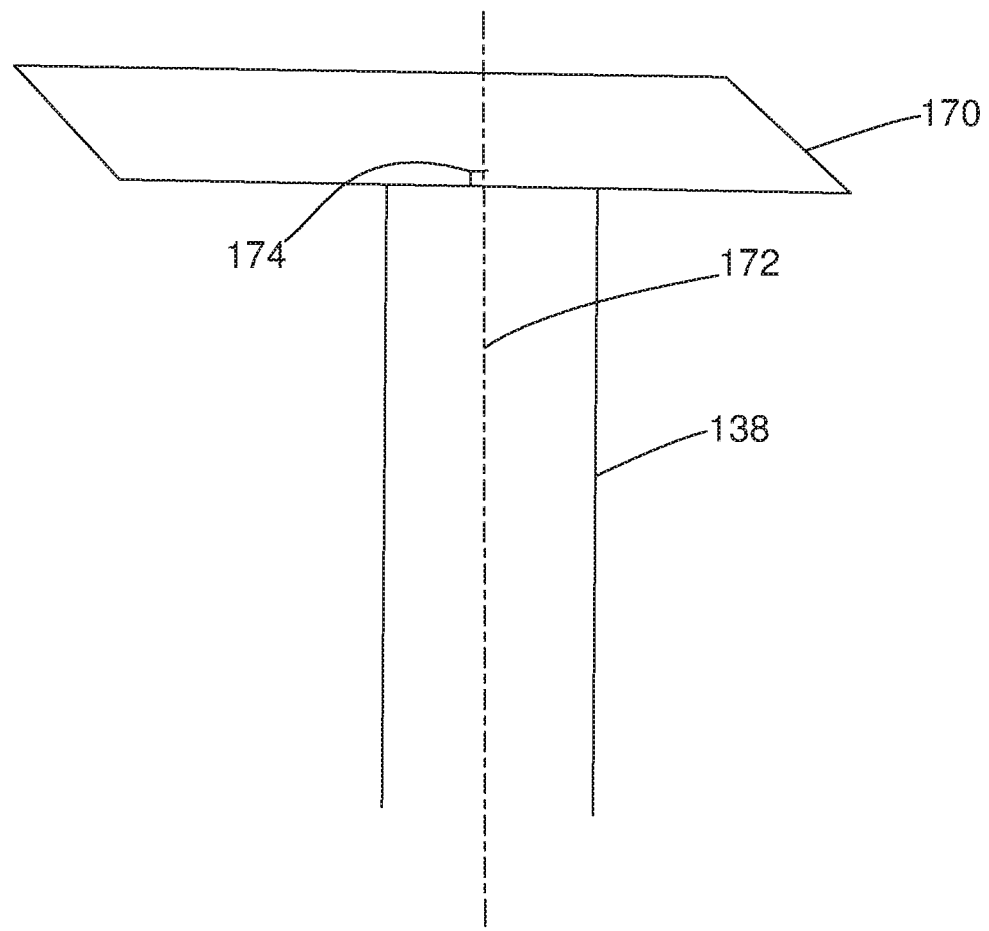
FIG. 7B illustrates the perpendicular relationship of a centerline of the seal of FIG. 7A to a plane.

This occurrence presents the situation shown in FIG. 7B, where a centerline 172 of the inner cylinder 138 of this example is perpendicular, per the right angle 174, with a plane 170. This plane 170 may be established by the outer surface of the wall portion 136. Alternatively, this plane 170 may not be established by a physical object but may exist in free space solely for the purpose of providing a geometrical relationship to the inner cylinder 138 and the centerline 172. As discussed above, the inner cylinder 138 may have a resting state that is center-aligned so that the centerline forms the right angle relative to the plane 170, as shown in FIG. 3 and as is maintained when the lead body 108 is also center-aligned as in FIG. 7A. Alternatively, the inner cylinder 138 may have a resting state that provides the centerline at a different angle relative to the same plane 170. This different angle of the resting state may correspond to the lead 108 being center-aligned or may correspond to a non-center-aligned lead body 108 such that the center-aligned lead body 108 may move the inner cylinder into a non-resting state position. In either case, radial movement of the lead 108 out of center-alignment may cause the centerline of the inner cylinder 138 to achieve yet another angle with respect to the plane 170.

Figure 8A:
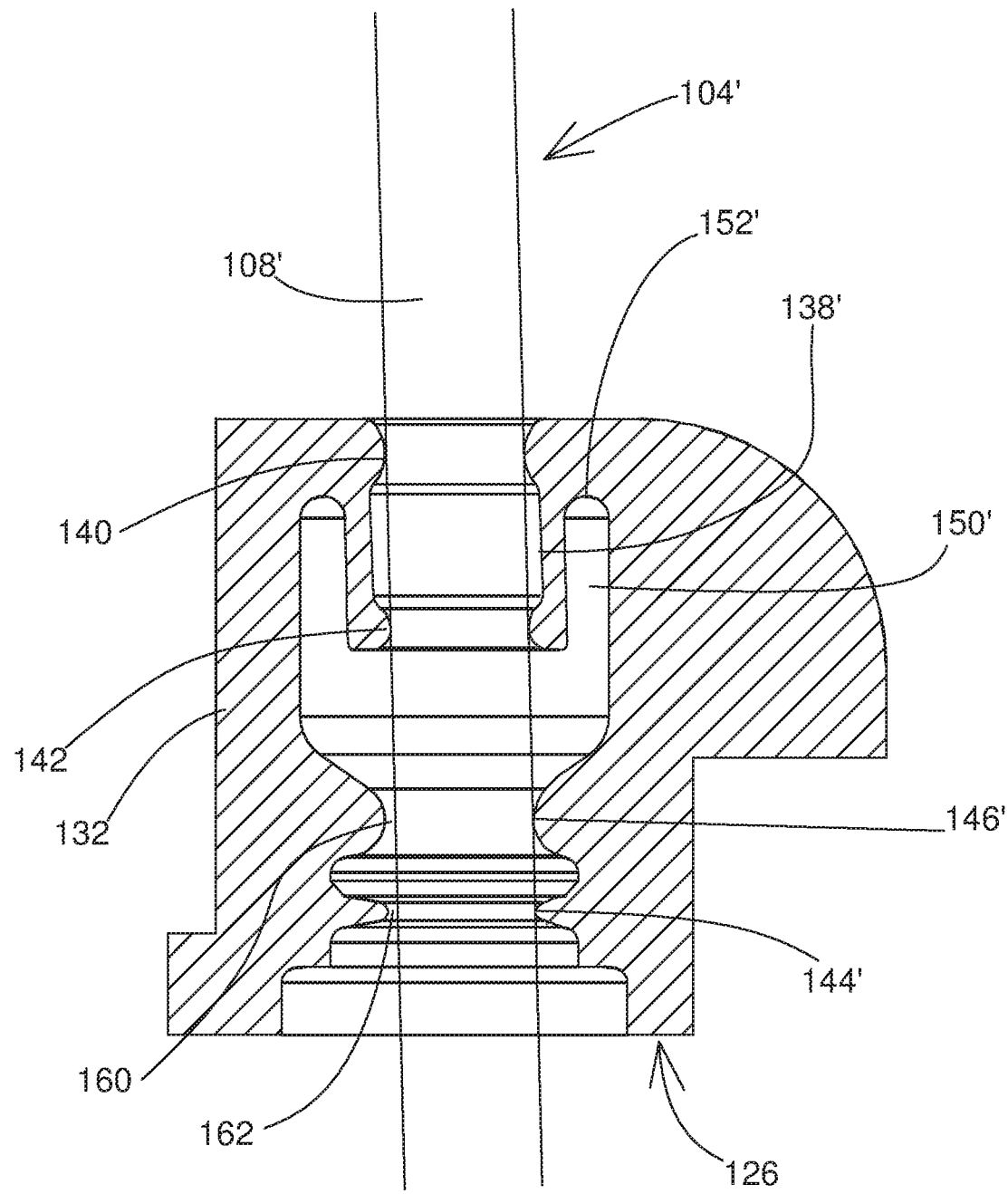
FIG. 8A shows a cross-sectional top view of the seal of FIG. 2 and further shows a lead body present within the seal where the lead body has moved out of center-alignment relative to a plane but remains engaged by the inner cylinder of the seal.

FIG. 8A shows the lead body 108' present within the front seal 126 but after having moved radially to no longer be center-aligned. In this case, it can be seen that small gaps 160, 162 have formed with respect to protrusions 144' and 146'. However, because the inner cylinder 138 has freedom of movement due to the free end, the compliant transition portion 152', and the gap 150' between the inner cylinder 138' and the outer cylinder of block 132, the inner cylinder 138 has remained fully engaged about the entire circumference of the lead body 108. In this example, both protrusion 140 and protrusion 142 have maintained the seal to the lead body 108.

Figure 8B:
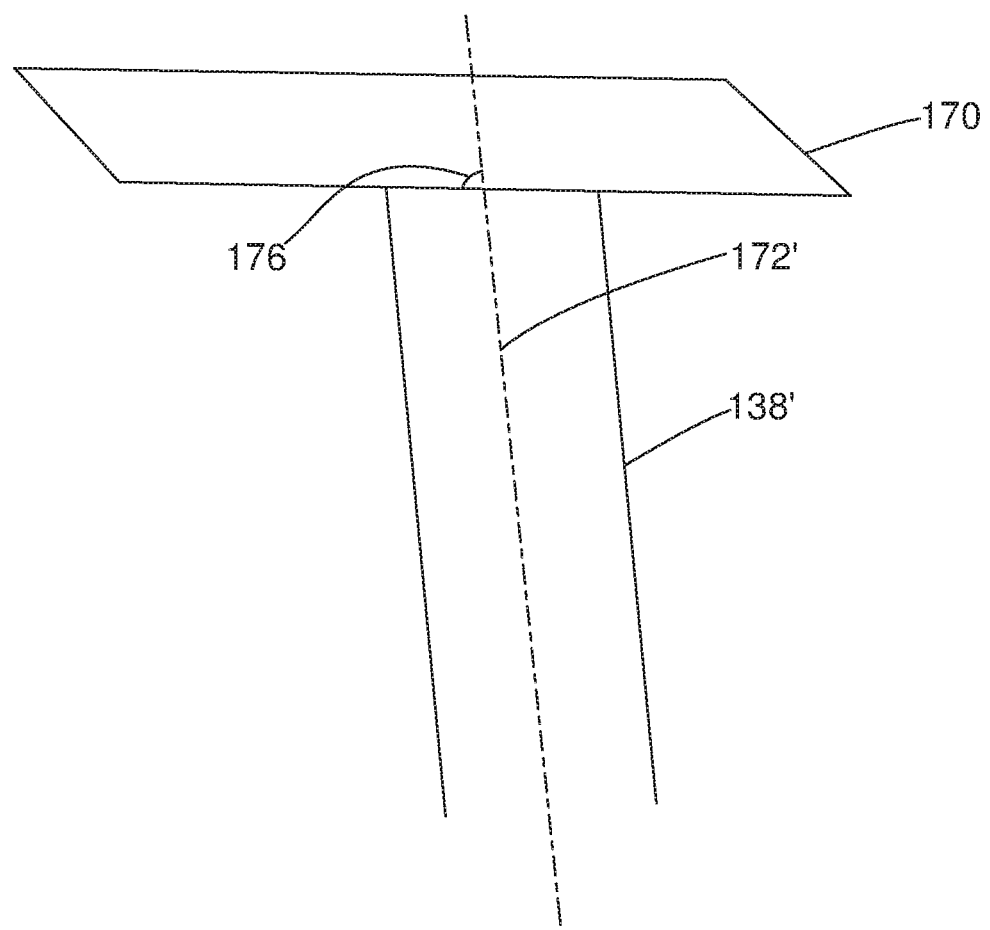
FIG. 8B illustrates the non-perpendicular relationship of the centerline of the seal of FIG. 8A to the plane.

This occurrence presents the situation shown in FIG. 8B, where the centerline 172' of the inner cylinder 138 of this particular example is no longer perpendicular, per the acute angle 176, with the plane 170. As discussed above, this plane 170 may be established by the outer surface of the wall portion 136. Alternatively, this plane 170 may not be established by a physical object but may exist in free space solely for the purpose of providing a geometrical relationship to the inner cylinder 138' and the centerline 172'.

While this discussion has been in relation to the front seal 126, it will be appreciated that a similar structure including the inner cylinder 138 may be used at other seal locations within the header 112. Furthermore, it will be appreciated that while the inner cylinder 138 is shown at the front of the front seal 126 to form the exterior opening 126, the seal orientation could be reversed where the inner cylinder 138 is positioned on the rear side of the front seal 126. It will additionally be appreciated that while this example shows a single inner cylinder 138, multiple inner cylinders could be used, such as an inner cylinder at the front of the front seal 126 as well as another inner cylinder at the rear of the front seal 126. Additional variations are discussed below in relation to FIGS. 9-24.

Figure 9:
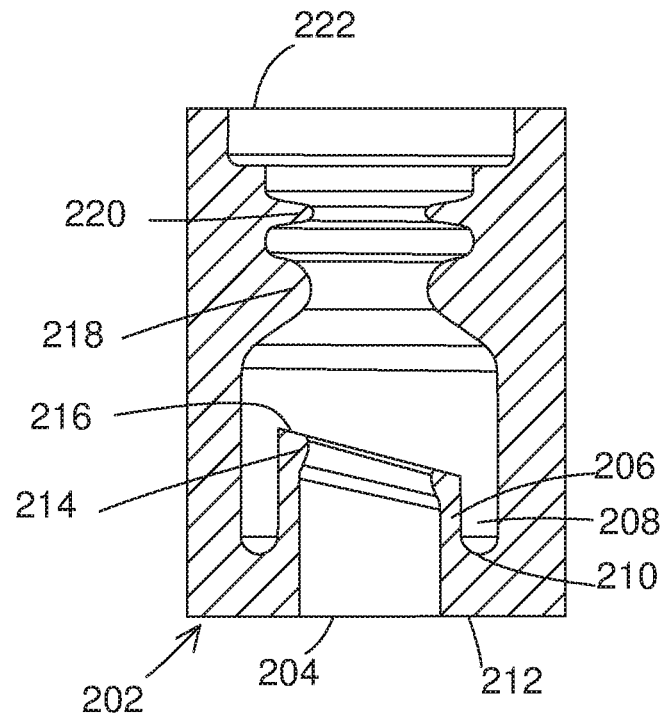
FIG. 9 shows a cross-sectional top view of a second example where the inner cylinder has an asymmetric rear edge while being coupled to a front wall portion.

FIG. 9 shows an example of a seal 202 that includes an inner cylinder 206 having a transition portion 210 at a front wall 212. The seal 202 defines the bore opening 204 and has a gap 208 between inner cylinder 206 and the outer cylinder formed by the seal body. The inner cylinder 206 of this example includes an inner protrusion 214 at a rear end. The rear end 216 of the inner cylinder 206 in this example is also asymmetric in that it is angled relative to a plane that is perpendicular to a centerline of the inner cylinder 206. This example also includes additional seals 218, 220 and defines a rear opening 222.

Figure 10:
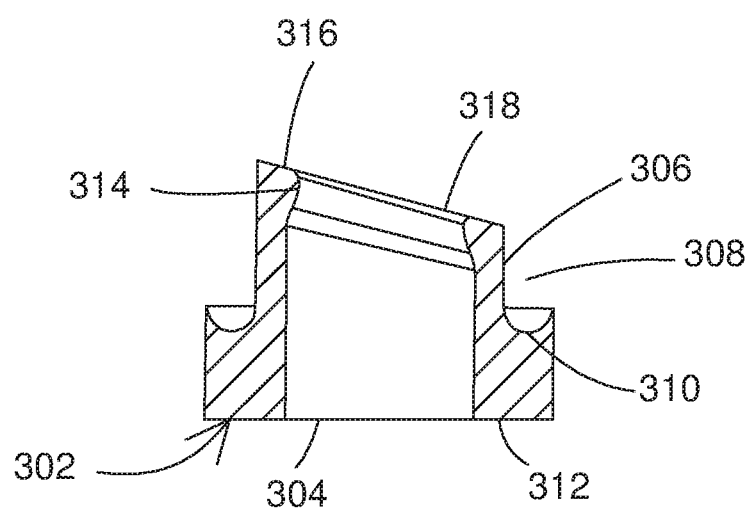
FIG. 10 shows a cross-sectional top view of a third example where the inner cylinder has an asymmetric rear edge while being coupled to a front wall portion and where no additional seals are present beyond the inner cylinder.

FIG. 10 shows an example of a seal 302 that includes an inner cylinder 306 having a transition portion 310 at a front wall 312. The seal 302 defines the bore opening 304 and has a gap 308 between the inner cylinder 306 and the header structure surrounding the seal body. The inner cylinder 306 of this example includes an inner protrusion 314 at a rear end. The rear end 316 of the inner cylinder 306 in this example is also asymmetric in that it is angled relative to a plane that is perpendicular to a centerline of the inner cylinder 306. This example lacks any additional seals and the inner cylinder 306 defines a rear opening 318 of the seal.

Figure 11:
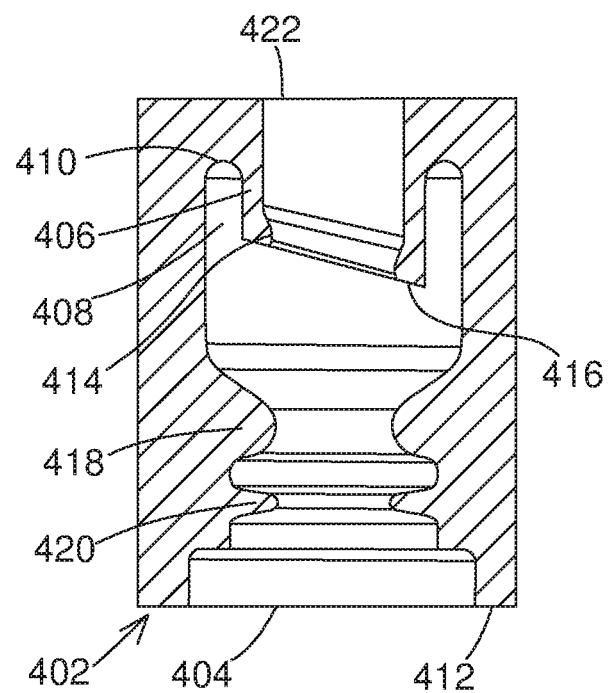
FIG. 11 shows a cross-sectional top view of a fourth example where the inner cylinder has an asymmetric front edge while being coupled to a rear wall portion.

FIG. 11 shows an example of a seal 402 that includes an inner cylinder 406 having a transition portion 410 at a rear wall. The front wall 412 of the seal 402 defines the bore opening 404. A gap 408 is formed between the inner cylinder 406 and the outer cylinder formed by the seal body. The inner cylinder 406 of this example includes an inner protrusion 414 at a front end 416. The front end 416 of the inner cylinder 406 in this example is also asymmetric in that it is angled relative to a plane that is perpendicular to a centerline of the inner cylinder 406. This example also includes additional seals 418, 420, and the inner cylinder 406 defines a rear opening 422 of the seal.

Figure 12:
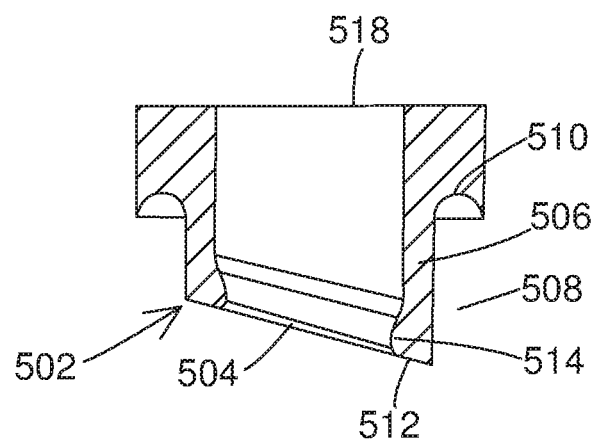
FIG. 12 shows a cross-sectional top view of a fifth example where the inner cylinder has an asymmetric front edge while being coupled to a rear wall portion and where no additional seals are present beyond the inner cylinder.

FIG. 12 shows an example of a seal 502 that includes an inner cylinder 506 having a transition portion 510 at a rear wall. The front end 512 of the inner cylinder 506 defines the bore opening 504. The seal 502 has a gap 508 between the inner cylinder 506 and the header structure surrounding the seal body. The inner cylinder 506 of this example includes an inner protrusion 514 at the front end 516. The front end 516 of the inner cylinder 506 in this example is also asymmetric in that it is angled relative to a plane that is perpendicular to a centerline of the inner cylinder 506. This example lacks any additional seals and the rear wall of the seal 502 defines a rear opening 518 of the seal.

Figure 13:
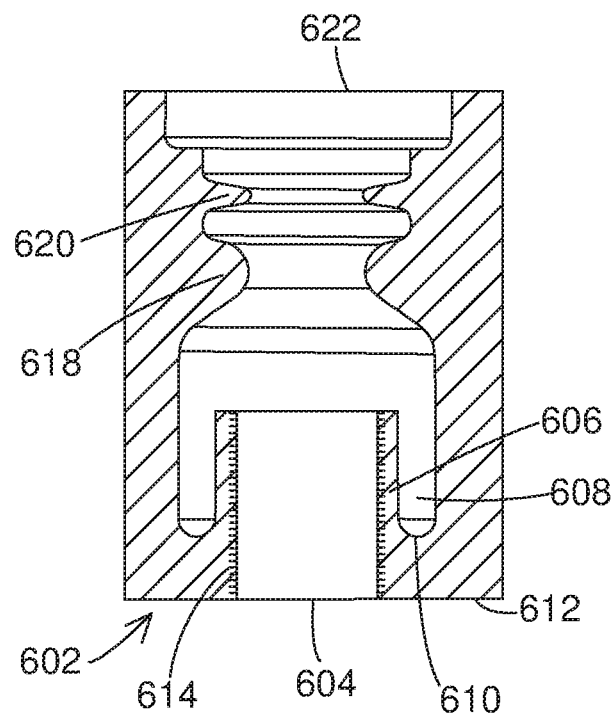
FIG. 13 shows a cross-sectional top view of a sixth example where the inner cylinder is coupled to a front wall and lacks an inner protrusion but has a surface coating.

FIG. 13 shows an example of a seal 602 that includes an inner cylinder 606 having a transition portion 610 at a front wall 612. The seal 602 defines the bore opening 604 and has a gap 608 between inner cylinder 606 and the outer cylinder formed by the seal body. The inner cylinder 606 of this example lacks an inner protrusion which results in a more complete contact over the length of the inner cylinder 606 to the lead body. To facilitate the ingress and egress of the lead body through the cylinder 606, the inner surface of the cylinder 606 may include a surface coating 614 to provide a lower friction. Examples of this surface coating include siloxane and parylene. As discussed above in relation to FIG. 1, rather than or in addition to the surface coating 614, the lead body 108 may include the surface coating 109 to reduce friction. This example also includes additional seals 618, 620 and defines a rear opening 622.

Figure 14:
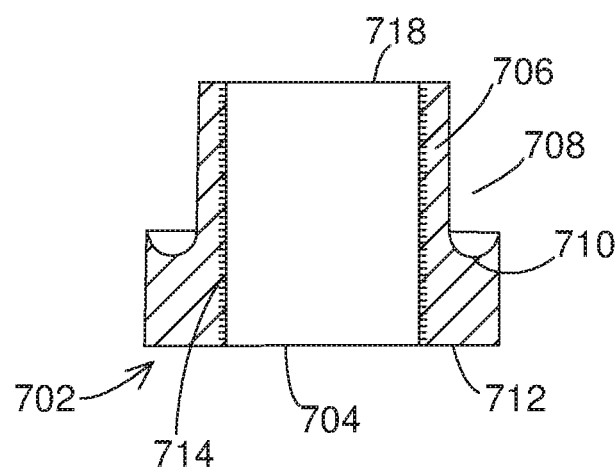
FIG. 14 shows a cross-sectional top view of a seventh example where no additional seals are present beyond the inner cylinder and where the inner cylinder is coupled to a front wall and lacks an inner protrusion but has a surface coating.

FIG. 14 shows an example of a seal 702 that includes an inner cylinder 706 having a transition portion 710 at a front wall 712. The seal 702 defines the bore opening 704 and has a gap 708 between the inner cylinder 706 and the header structure surrounding the seal body. The inner cylinder 706 of this example lacks an inner protrusion which results in a more complete contact over the length of the inner cylinder 706 to the lead body. To facilitate the ingress and egress of the lead body through the cylinder 706, the inner surface of the cylinder 706 may include a surface coating 714 like the surface coating 614 of FIG. 13 to provide a lower friction. As discussed above in relation to FIGS. 1 and 13, rather than or in addition to the surface coating 714, the lead body 108 may include the surface coating 109 to reduce friction. This example lacks any additional seals and the inner cylinder 706 defines a rear opening 718 of the seal.

Figure 15:
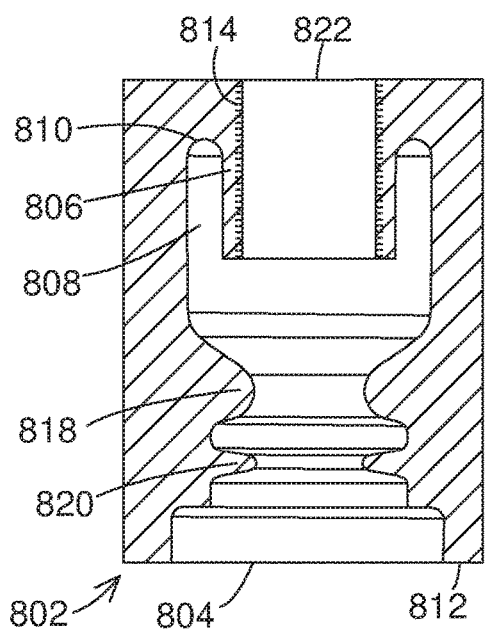
FIG. 15 shows a cross-sectional top view of an eighth example where the inner cylinder is coupled to a rear wall and lacks an inner protrusion but has a surface coating.

FIG. 15 shows an example of a seal 802 that includes an inner cylinder 806 having a transition portion 810 at a rear wall. The front wall 812 of the seal 802 defines the bore opening 804. A gap 808 is formed between the inner cylinder 806 and the outer cylinder formed by the seal body. The inner cylinder 806 of this example lacks an inner protrusion which results in a more complete contact over the length of the inner cylinder 806 to the lead body. To facilitate the ingress and egress of the lead body through the cylinder 806, the inner surface of the cylinder 806 may include a surface coating 814 like the surface coating 614 of FIG. 13 to provide a lower friction. As discussed above in relation to FIGS. 1 and 13, rather than or in addition to the surface coating 814, the lead body 108 may include the surface coating 109 to reduce friction. This example also includes additional seals 818, 820, and the inner cylinder 806 defines a rear opening 822 of the seal.

Figure 16:
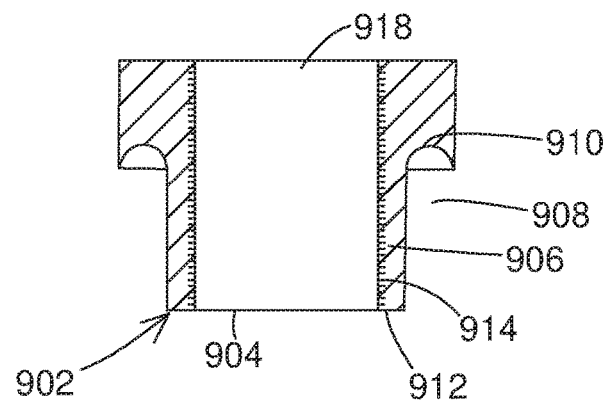
FIG. 16 shows a cross-sectional top view of a ninth example where no additional seals are present beyond the inner cylinder and where the inner cylinder is coupled to a rear wall and lacks an inner protrusion but has a surface coating.

FIG. 16 shows an example of a seal 902 that includes an inner cylinder 906 having a transition portion 910 at a rear wall. The front end 912 of the inner cylinder 906 defines the bore opening 904. The seal 902 has a gap 908 between the inner cylinder 906 and the header structure surrounding the seal body. The inner cylinder 906 of this example lacks an inner protrusion which results in a more complete contact over the length of the inner cylinder 906 to the lead body. To facilitate the ingress and egress of the lead body through the cylinder 906, the inner surface of the cylinder 906 may include a surface coating 914 like the surface coating 614 of FIG. 13 to provide a lower friction. As discussed above in relation to FIGS. 1 and 13, rather than or in addition to the surface coating 914, the lead body 108 may include the surface coating 109 to reduce friction. This example lacks any additional seals and the rear wall of the seal 902 defines a rear opening 918 of the seal.

Figure 17:
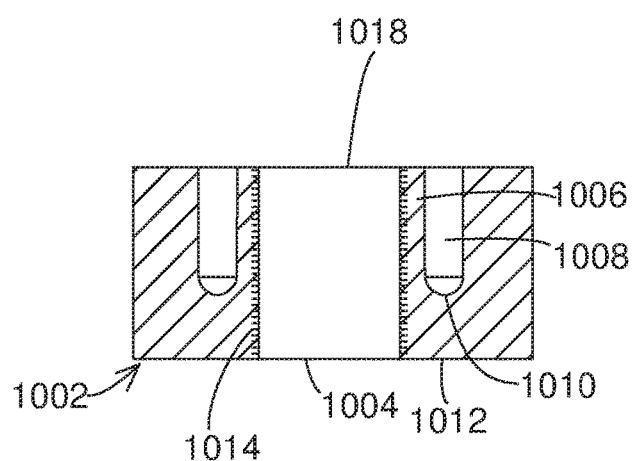
FIG. 17 shows a cross-sectional top view of a tenth example where no additional seals are present beyond the inner cylinder but where a full-length outer cylinder is present and where the inner cylinder is coupled to a front wall and lacks an inner protrusion but has a surface coating.

FIG. 17 shows an example of a seal 1002 that includes an inner cylinder 1006 that extends the full-length of the seal 1002 and where the outer cylinder surrounds the inner cylinder 1006 over the full length of the seal 1002. The inner cylinder 1006 has a transition portion 1010 at a front wall 1012. The seal 1002 defines the bore opening 1004 and has a gap 1008 between the inner cylinder 1006 and the outer cylinder surrounding the seal body. The inner cylinder 1006 of this example lacks an inner protrusion which results in a more complete contact over the length of the inner cylinder 1006 to the lead body. To facilitate the ingress and egress of the lead body through the cylinder 1006, the inner surface of the cylinder 1006 may include a surface coating 1014 like the surface coating 614 of FIG. 13 to provide a lower friction. As discussed above in relation to FIGS. 1 and 13, rather than or in addition to the surface coating 1014, the lead body 108 may include the surface coating 109 to reduce friction. This example lacks any additional seals and the inner cylinder 1006 defines a rear opening 1018 of the seal although it is present within the full-length outer cylinder.

Figure 18:
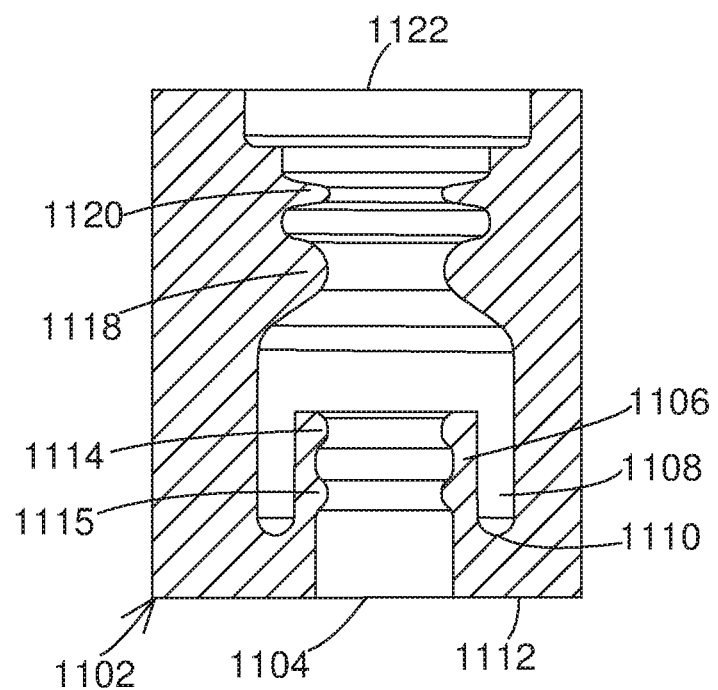
FIG. 18 shows a cross-sectional top view of an eleventh example where the inner cylinder is coupled to a front wall and has multiple inner protrusions including an inner protrusion at an intermediate location.

FIG. 18 shows an example of a seal 1102 that includes an inner cylinder 1106 having a transition portion 1110 at a front wall 1112. The seal 1102 defines the bore opening 1104 and has a gap 1108 between inner cylinder 1106 and the outer cylinder formed by the seal body. The inner cylinder 1106 of this example includes a first inner protrusion 1114 at a rear end and has a second inner protrusion 1115 at an intermediate location to provide an additional sealing surface. It will be appreciated that any number of additional inner protrusions may be included, such as a providing a third inner protrusion at the opening 1104. This example also includes additional seals 1118, 1120 and defines a rear opening 1122.

Figure 19:
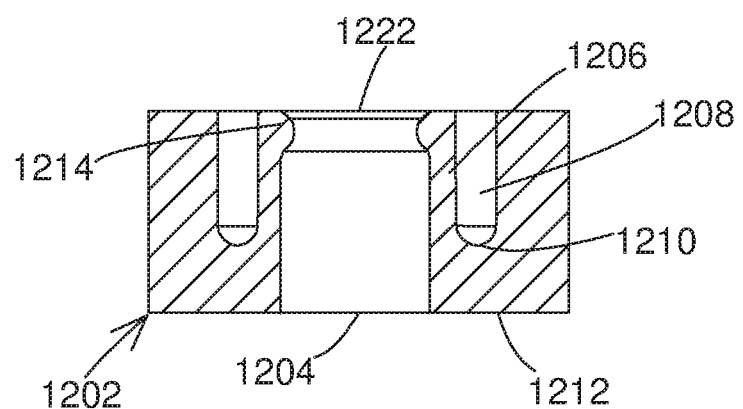
FIG. 19 shows a cross-sectional top view of a twelfth example where no additional seals are present beyond the inner cylinder but where a full-length outer cylinder is present and where the inner cylinder is coupled to a front wall and includes a rear protrusion.

FIG. 19 shows an example of a seal 1202 that includes an inner cylinder 1206 and where the outer cylinder surrounding the inner cylinder 1206 is a full length of the seal 1202. The inner cylinder 1206 has a transition portion 1210 at a front wall 1212. The seal 1202 defines the bore opening 1204 and has a gap 1208 between the inner cylinder 1206 and the outer cylinder surrounding the seal body. The inner cylinder 1206 of this example includes an inner protrusion 1214 at a rear end. This example lacks any additional seals and the inner cylinder 1206 defines a rear opening 1222 of the seal.

Figure 20:
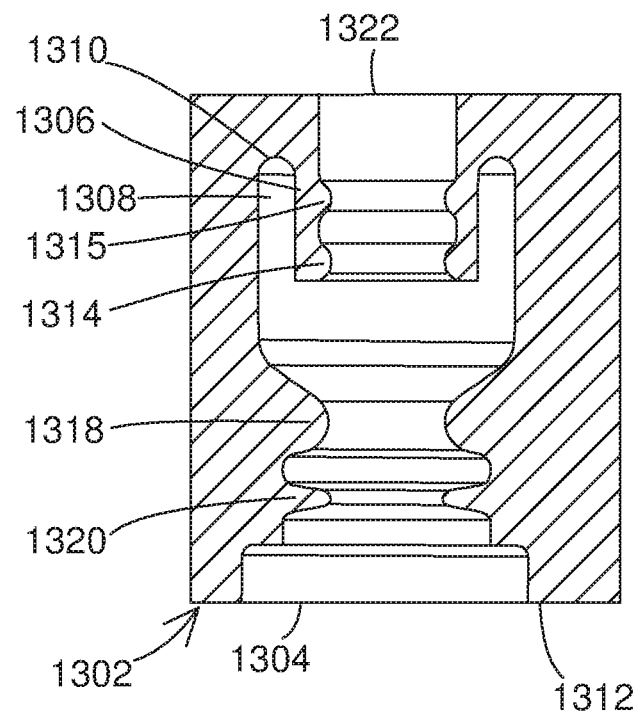
FIG. 20 shows a cross-sectional top view of a thirteenth example where the inner cylinder is coupled to a rear wall and has multiple inner protrusions including an inner protrusion at an intermediate location.

FIG. 20 shows an example of a seal 1302 that includes an inner cylinder 1306 having a transition portion 1310 at a rear wall. The front wall 1312 of the seal 1302 defines the bore opening 1304. A gap 1308 is formed between the inner cylinder 1306 and the outer cylinder formed by the seal body. The inner cylinder 1306 of this example includes a first inner protrusion 1314 at a front end and has a second inner protrusion 1315 at an intermediate location to provide an additional sealing surface. It will be appreciated that any number of additional inner protrusions may be included, such as a providing a third inner protrusion at the opening 1322. This example also includes additional seals 1318, 1320, and the inner cylinder 1306 defines a rear opening 1322 of the seal.

Figure 21:
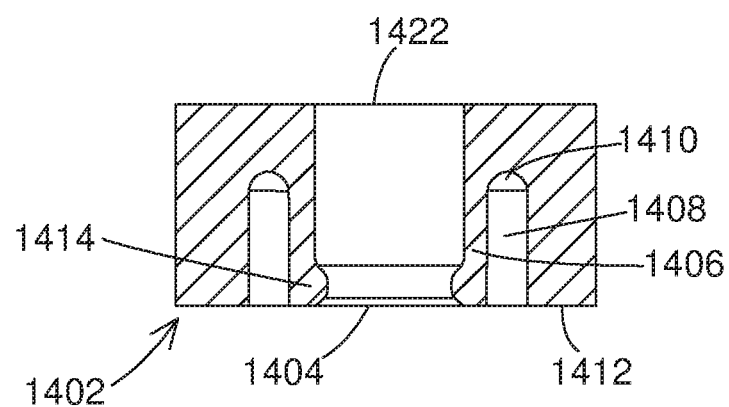
FIG. 21 shows a cross-sectional top view of a fourteenth example where no additional seals are present beyond the inner cylinder but where a full-length outer cylinder is present and where the inner cylinder is coupled to a front wall and includes a front protrusion.

FIG. 21 shows an example of a seal 1402 that includes an inner cylinder 1406 and where the outer cylinder surrounding the inner cylinder 1406 is a full length of the seal 1402. The inner cylinder 1406 has a transition portion 1410 at a rear wall. The inner cylinder 1406 defines the bore opening 1404 and has a gap 1408 between the inner cylinder 1406 and the outer cylinder surrounding the seal body. The inner cylinder 1406 of this example includes an inner protrusion 1414 at a front end. This example lacks any additional seals and the inner cylinder 1406 also defines a rear opening 1422 of the seal.

Figure 22:
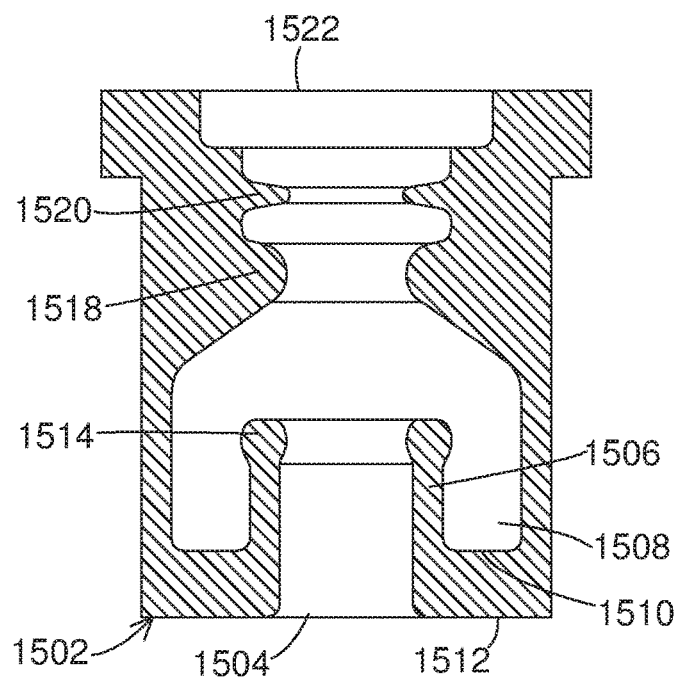
FIG. 22 shows a cross-sectional top view of a fifteenth example where the inner cylinder is coupled to a rear wall and has a hinge point on the wall portion that is further separated from the outer cylinder.

FIG. 22 shows an example of a seal 1502 that includes an inner cylinder 1506 having a transition portion 1510 at a front wall 1512. The transition portion 1510 of this example creates a relatively large gap 1508 from the inner cylinder 1506 to the outer cylinder at the hinge point of the inner cylinder 1506 provided by the transition portion 1510. The seal 1502 defines the bore opening 1504. The inner cylinder 1506 of this example includes an inner protrusion 1514 at a rear end. This example also includes additional seals 1518, 1520 and defines a rear opening 1522. Like examples described above, the seal configuration may also be reversed so that the inner cylinder 1506 is preset at the rear of the seal rather than the front. Furthermore, the large space provided by the transition portion 1510 may be provided where only the inner cylinder 1506 provides the seal to the lead body and where additional seals like seals 1518 and 1520 are omitted.

Figure 23:
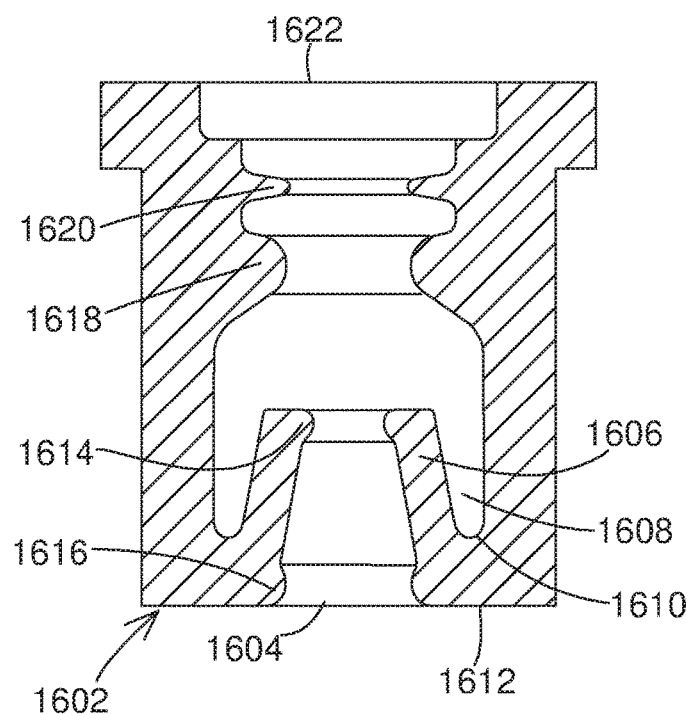
FIG. 23 shows a cross-sectional top view of a sixteenth example where the inner cylinder is coupled to a rear wall and has a diameter that varies along the length.

FIG. 23 shows an example of a seal 1602 that includes an inner cylinder 1606 having a transition portion 1610 at a front wall 1612. The inner cylinder 1606 of this example includes a diameter that varies over the length of the inner cylinder 1606. As can be seen in this specific example, the diameter varies by continuously decreasing from the front end to the rear end of the inner cylinder 1606, but it will be appreciated that the diameter may vary over the length in any number of ways such as being a smallest diameter at an intermediate location or at the front end. This specific example may produce a tighter fitting seal to the lead body 108 at the protrusion 1614. The seal 1602 defines the bore opening 1604 and has a gap 1608 between inner cylinder 1606 and the outer cylinder formed by the seal body. The inner cylinder 1606 of this example includes a first inner protrusion 1614 at a rear end and a second inner protrusion 1616 at the front end where the bore opening 1604 is provided. This example also includes additional seals 1618, 1620 and defines a rear opening 1622. Like examples described above, the seal configuration may also be reversed so that the inner cylinder 1606 is preset at the rear of the seal rather than the front. Furthermore, the varying diameter of the inner cylinder 1606 may be provided where only the inner cylinder 1606 provides the seal to the lead body and where additional seals like seals 1518 and 1520 are omitted.

FIG. 24 shows an example of a seal 1702 that includes an inner cylinder 1706 having a transition portion 1710 at a front wall 1712. The transition portion 1710 of this example creates a relatively large gap 1708 from the inner cylinder 1706 to the outer cylinder at the hinge point of the inner cylinder 1706 provided by the transition portion 1710 like that of FIG. 22. However, in this example, the inner cylinder 1706 forms an inversion 1716 and result in an innermost cylinder portion 1707 defining an opening 1705 and a second opening 1709. This innermost cylinder portion 1707 may produce a tighter seal to the lead body 108. The inner cylinder 1706 of this example includes an inner protrusion 1714 at a rear end. The inversion 1716 may exist in the resting state of the seal 1702, or as discussed below, the inversion 1716 may be produced by movement of the lead body through the inner cylinder 1706. The seal 1702 defines the bore opening 1704. This example also includes additional seals 1718, 1720 and defines a rear opening 1722. Like examples described above, the seal configuration may also be reversed so that the inner cylinder 1706 is preset at the rear of the seal rather than the front. Furthermore, the large space provided by the transition portion 1710 may be provided where only the inner cylinder 1706 provides the seal to the lead body and where additional seals like seals 1718 and 1720 are omitted.

As discussed above, the inversion may exist in the resting state of the seal 1702 or may be created by movement of the lead body. In the example where the inversion is created by movement of the lead body for the orientation shown in FIG. 24 where the inner cylinder 1716 forms the bore opening 1704, the seal 1702 may be in a resting state with the lead 104 being fully inserted. In this resting state, the inversion 1716 does not exist so that only the inner cylinder 1706 is present. However, upon movement in the direction of egress, the movement of the lead body 108 pulls the inner cylinder 1716 to form the inversion 1716 and the innermost cylinder 1707.

In the orientation opposite of that shown in FIG. 24, where the inner cylinder 1716 forms the rear opening of the seal, the seal 1702 may be in a resting state before the lead 104 is inserted. In this resting state, the inversion 1716 does not exist so that only the inner cylinder 1706 is present. Upon insertion of the lead 104 and movement of the lead 104 through the inner cylinder 1706 in the direction of ingress, the movement of the lead body 108 pulls the inner cylinder 1716 to form the inversion 1716 and the innermost cylinder 1707.

FIG. 25 shows an example of a seal 1802 that includes an inner cylinder 1806 having a transition portion 1810 at a front wall 1812. The seal 1802 defines the bore opening 1804 and has a gap 1808 between inner cylinder 1806 and the outer cylinder 1801 formed by the seal body. The inner cylinder 1806 of this example includes an inner protrusion 1814 at a rear end. This example also includes additional seals 1818, 1820 and defines a rear opening 1822. Like examples described above, the seal configuration may also be reversed so that the inner cylinder 1806 is preset at the rear of the seal rather than the front. Furthermore, the space provided by the transition portion 1810 may be provided where only the inner cylinder 1806 provides the seal to the lead body and where additional seals like seals 1818 and 1820 are omitted.

Of particular note in FIG. 25, the outer cylinder 1801 and/or at least a portion of the wall portion of the seal 1802 is constructed of a first material having a first modulus of elasticity value while the inner cylinder 1806 is constructed of a second material having a second modulus of elasticity value. For instance, in one example the outer cylinder 1801 as well as at least a portion of the wall portion, may have a modulus value above 700 pounds per square inch while the inner cylinder 1806 may have a modulus of elasticity value below 700 pounds per square inch, such as specified in the Dow Corning datasheet previously introduced. In cases where two different materials are used, the outer cylinder 1801 and/or at least a portion of the wall portion may have a modulus of elasticity value that far exceeds the range of modulus of elasticity values of the inner cylinder 1806 previously specified, such as where the inner cylinder modulus of elasticity value continues to fall within the previously introduced range of 100-1000 pounds per square while the outer cylinder 1801 and/or at least a portion of the wall portion may have a modulus of elasticity value that exceeds 10,000 pounds per square inch. The two materials are joined at the junction 1824, and the outer cylinder 1801 forms additional wall area 1826, where the wall portion 1812 has a modular of elasticity value than the modulus of elasticity value of the wall portion 1826. One manner of bonding the two materials together includes utilizing a primer such as a siloxane coating topped with a silicone medical adhesive to then allow the second material to be overmolded into the interior of the outer cylinder 1801 to form the inner cylinder 1806.

FIG. 26 shows an example of a front portion of a header 1900 of an implantable medical device. The header 1900 includes a header body 1901 typically constructed of a rigid biocompatible polymer such as polysulfone or polyether ether ketone (PEEK). The seal 1902 is present within a lead bore 1928 of the header body 1901. In this example, there is no outer cylinder and a wall portion 1912 of the seal 1902 is directly bonded to the cylindrical wall of the lead bore 1928. This example also shows an additional alternative where the header body 1901 has been coated with a layer 1926 of an elastic material like silicone that also enters the lead bore 1928 to form the seal 1902. The lead bore 1928 and/or the exterior of the lead body 1901 may be coated in a primer such as siloxane topped with silicone medical adhesive to allow bonding of the coating that forms the layer 1926 and seal 1902.

This example of the seal 1902 that includes an inner cylinder 1906 having a transition portion 1910 at a front wall 1912. The seal 1902 defines the bore opening 1904 and has a gap 1908 between inner cylinder 1906 and the lead bore 1928. The inner cylinder 1906 of this example includes an inner protrusion 1914 at a rear end. This example omits any additional seals but those may be included as an alternative. Like examples described above, the seal configuration may also be reversed so that the inner cylinder 1906 meets the transition portion 1910 at the rear of the seal 1902 rather than the front.

The embodiments described above in FIGS. 1-26 also apply to lead extensions in addition to device headers. For instance, lead extensions may include a distal end that forms a housing that provides a lead bore containing electrical connectors much like a device header. The proximal end of the lead may be inserted into the lead bore of the extension in the same manner as inserting the lead into the lead bore of a device header. Therefore, any discussion of utilizing a seal within a lead bore of a device header as discussed herein should be considered to also apply to utilizing a seal within a lead bore of a lead extension. Furthermore, the proximal end of a lead extension is inserted into the lead bore of the device header and therefore the seal of the device header may operate in conjunction with the lead body of the lead extension to form a seal in the same manner as if a lead had been inserted into the lead bore of the device header.

While embodiments have been particularly shown and described, it will be understood by those skilled in the art that various other changes in the form and details may be made therein without departing from the spirit and scope of the invention.

What is claimed is:

1. A seal for an implantable medical device, comprising:
   a body comprising:
   a first cylinder that is elastic and that defines a seal bore having a centerline, the first cylinder having an outer diameter; and
   a wall portion that is coupled to the first cylinder and that has an outer surface that forms a plane that the centerline intersects, the first cylinder being movable relative to the wall portion to allow an angle of intersection between the centerline and the plane to change.

2. The seal of claim 1, further comprising a protrusion that is present about a circumference of the seal bore and extends radially inward into the seal bore.

3. The seal of claim 1, further comprising a second cylinder coupled to the wall portion, the second cylinder defining an outer seal bore having an inner diameter larger than the outer diameter of the first cylinder such that the second cylinder surrounds the first cylinder.

4. The seal of claim 3, wherein the second cylinder extends beyond an end of the first cylinder, and wherein the second cylinder further comprises a protrusion that is present about a circumference of the outer seal bore and extends radially inwardly into the outer seal bore.

5. The seal of claim 3, wherein the first cylinder and the second cylinder are concentric.

6. The seal of claim 1, wherein the at least the first cylinder of the body has a modulus of elasticity value ranging from 100 to 1000 pounds per square inch.

7. The seal of claim 6, wherein at least the first cylinder of the body has a modulus of elasticity value ranging from 400 to 700 pounds per square inch.

8. The seal of claim 1, wherein the at least the first cylinder of the body comprises silicone.

9. The seal of claim 1, wherein at least the first cylinder of the body comprises urethane.

10. The seal of claim 1, wherein the first cylinder comprises a first material and at least a portion of the wall portion comprises a second material, and wherein the first material has a lower modulus of elasticity value than the second material.

11. An implantable medical device, comprising:
    a housing defining a lead bore having a lead bore diameter;
    circuitry within the housing;
    an electrical connector positioned within the lead bore and electrically coupled to the circuitry; and
    a seal body coupled to the housing, the seal body comprising:
    a first cylinder that is elastic and that defines a seal bore having a centerline, the first cylinder being positioned within the lead bore and having an outer diameter that is smaller than the lead bore diameter at a position of the first cylinder; and
    a wall portion that is coupled to the housing, the wall portion being coupled to the first cylinder and having an outer surface that forms a plane that the centerline intersects, the first cylinder being movable relative to the wall portion to allow an angle of intersection between the centerline and the plane to change.

12. The implantable medical device of claim 11, wherein the seal body further comprises a protrusion that is present about a circumference of the seal bore and extends radially inward into the seal bore.

13. The implantable medical device of claim 11, wherein the seal body further comprises a second cylinder coupled to the wall portion, the second cylinder defining an outer seal bore having an inner diameter larger than the outer diameter of the first cylinder such that the second cylinder surrounds the first cylinder.

14. The implantable medical device of claim 13, wherein the second cylinder extends beyond an end of the first cylinder, and wherein the second cylinder further comprises a protrusion that is present about a circumference of the outer seal bore and extends radially inward into the outer seal bore.

15. The implantable medical device of claim 13, wherein the first cylinder and the second cylinder are concentric.

16. The implantable medical device of claim 11, wherein at least the first cylinder of the elastic seal body has a modulus of elasticity value ranging from 100 to 1000 pounds per square inch.

17. The implantable medical device of claim 16, wherein at least the first cylinder of the elastic seal body has a modulus of elasticity value ranging from 400 to 700 pounds per square inch.

18. The implantable medical device of claim 11, wherein at least the first cylinder of the seal body comprises silicone.

19. The implantable medical device of claim 11, wherein at least the first cylinder of the seal body comprises urethane.

20. The implantable medical device of claim 11, wherein the first cylinder is positioned at a front of the seal body.

21. The implantable medical device of claim 11, wherein the first cylinder is positioned at a rear of the seal body.

22. The implantable medical device of claim 11, wherein the first cylinder comprises a diameter that varies over a length of the first cylinder.

23. The implantable medical device of claim 11, wherein the first cylinder comprises an inversion.

24. The implantable medical device of claim 11, wherein the first cylinder comprises multiple protrusions extending radially inward into the seal bore.

25. The implantable medical device of claim 11, wherein the first cylinder comprises an asymmetric front end.

26. The implantable medical device of claim 11, wherein the first cylinder comprises an asymmetric rear end.

27. The implantable medical device of claim 11, wherein the first cylinder comprises a surface coating.

28. The implantable medical device of claim 11, wherein the second cylinder is less than a full length of the seal body.

29. The implantable medical device of claim 11, wherein the seal body comprises a flange.

30. The implantable medical device of claim 11, wherein the first cylinder comprises a first material and at least a portion of the wall portion comprises a second material, and wherein the first material has a lower modulus of elasticity value than the second material.

31. A seal for an implantable medical device, comprising:
    a body comprising:

a first cylinder that is elastic and that defines a seal bore having a centerline, the first cylinder having an outer diameter; and a wall portion that is coupled to the first cylinder with the first cylinder having a resting position where the centerline forms a first angle with respect to a first plane, the first cylinder being movable relative to the wall portion to allow the first angle of the centerline with respect to the first plane to change.

32. An implantable medical device, comprising:

a housing defining a lead bore having a lead bore diameter;

circuitry within the housing;

an electrical connector positioned within the lead bore and electrically coupled to the circuitry; and a seal body coupled to the housing, the seal body comprising:

a first cylinder that is elastic and that defines a seal bore having a centerline, the first cylinder being positioned within the lead bore and having an outer diameter that is smaller than the lead bore diameter at a position of the first cylinder; and a wall portion that is coupled to the housing, the wall portion being coupled to the first cylinder with the first cylinder having a resting position where the centerline forms a first angle with respect to a first plane, the first cylindrical portion being movable relative to the wall portion to allow the first angle of the centerline with respect to the first plane to change.

* * * * *